US009029127B2

(12) United States Patent
Garcia et al.

(10) Patent No.: US 9,029,127 B2
(45) Date of Patent: May 12, 2015

(54) METHOD OF DEGRADING TBP USING A PHOTOSYNTHETIC BACTERIAL STRAIN

(75) Inventors: Daniel Garcia, Saint Martin de la Brasque (FR); Cécile Berne, Saint Paul Lez Durance (FR)

(73) Assignee: Commissariat a l'Energie Atomique, Paris (FR)

( * ) Notice: Subject to any disclaimer, the term of this patent is extended or adjusted under 35 U.S.C. 154(b) by 2521 days.

(21) Appl. No.: 10/556,324

(22) PCT Filed: May 13, 2004

(86) PCT No.: PCT/FR2004/001165
§ 371 (c)(1),
(2), (4) Date: Aug. 21, 2006

(87) PCT Pub. No.: WO2004/101449
PCT Pub. Date: Nov. 25, 2004

(65) Prior Publication Data
US 2008/0145917 A1  Jun. 19, 2008

(30) Foreign Application Priority Data
May 14, 2003  (FR) ..................................... 03 05762

(51) Int. Cl.
B08B 3/00 (2006.01)
B01D 15/00 (2006.01)
C09D 189/00 (2006.01)
C02F 3/34 (2006.01)
C12N 1/21 (2006.01)
A01N 25/10 (2006.01)
A01N 37/46 (2006.01)
A01N 63/02 (2006.01)
C07K 14/80 (2006.01)

(52) U.S. Cl.
CPC . *C02F 3/34* (2013.01); *A01N 25/10* (2013.01); *A01N 37/46* (2013.01); *A01N 63/02* (2013.01); *C07K 14/80* (2013.01)

(58) Field of Classification Search
CPC ....... A01N 25/10; A01N 37/46; A01N 63/02; C09D 5/14; C09D 5/1637; C09D 7/1233; C09D 7/125; C09D 5/1625; C09D 189/00; C09D 5/00; C09D 5/30; C09D 5/008; C09D 7/1291; C08L 89/00; C12N 15/102; C12N 15/1027; C12N 15/8241
See application file for complete search history.

(56) References Cited

U.S. PATENT DOCUMENTS 5,453,375 A   9/1995   Stoner et al.
6,106,719 A   8/2000   Sawayama

FOREIGN PATENT DOCUMENTS

FR   2 712 604 A    5/1995
JP   59 173197 A   10/1984
JP   2003089997 A * 3/2003

OTHER PUBLICATIONS

Min-Kyung et al., "Regulation of benzoate-CoA ligase in *Rhodopseudomonas palustris*", FEMS Microbiology Letters, vol. 83, 1991, pp. 199-204.
F.W. Larimer et al., "Complete genome sequence of the metabolically versatile photosynthetic bacterium *Rhodopseudomonas palustris*", Nature Biotechnology, vol. 22, No. 1, Jan. 2004, pp. 55-61.
Thomas et al., "Biodegradation of Tributyl Phosphate by Naturally Occurring Microbial Isolates and Coupling to the Removal of Uranium from Aqueous Solution", Environmental Science and Technology, American Chemical Society, vol. 30, No. 7, Jul. 1, 1996, pp. 2371-2375.

* cited by examiner

*Primary Examiner* — Debbie K Ware
(74) *Attorney, Agent, or Firm* — Alston & Bird LLP

(57) ABSTRACT

The invention relates to: a method of treating liquid waste (liquid agricultural or industrial effluents or aquatic sites) which is loaded or polluted with tributyl phosphate (TBP), modified bacterial strains which can be used in the aforementioned treatment method, a method for monitoring changes in TBP pollution, and the device which is used to perform said treatment method. According to the invention, the liquid waste-treatment or -purification method essentially comprises: steps (1) consisting in bringing said liquid waste into contact with at least one non-sulphur purple photosynthetic bacterial strain which is resistant to TBP and which is selected from the group containing *Rhodopseudomonas palustris (Rp. palustris)*, *Rhodospirillum rubrum (Rs. rubrum)*, *Rhodobacter capsulatus (Rb. capsulatus)* or *Rhodobacter sphaeroides (Rb. Sphaeroides)* as well as the aforementioned modified bacterial strains in order to overexpress cytochrome P450 in conditions that enable the degradation of the TBP present in said waste, regardless of the initial TBP concentration; and (2) the recovery of the purified liquid effluents.

14 Claims, 10 Drawing Sheets

METHOD OF DEGRADING TBP USING A PHOTOSYNTHETIC BACTERIAL STRAIN

CROSS-REFERENCE TO RELATED APPLICATIONS

This application is a 371 National Phase Application of PCT/FR04/01165, filed May 13, 2004.

BACKGROUND OF THE INVENTION

The present invention relates to a method of treating liquid waste (liquid agricultural or industrial effluents or aquatic sites) loaded or polluted with tributyl phosphate (TBP), to modified bacterial strains which can be used in said treatment method, to a method of monitoring changes in TBP pollution, and to a device which is used to carry out said treatment method.

Tributyl phosphate (TBP) is an organophosphorus compound used in many industrial fields, and in particular: as a solvent in the recycling of nuclear fuel and in the purification of rare metals or in the manufacture of plasticizers, hydraulic fluids, pesticides, herbicides, antifoaming agents or anticorrosive agents.

All these applications generate large amounts of waste, which is relatively non-biodegradable, since TBP is barely degraded or not at all, in a natural environment: it is barely degraded by indigenous microorganisms and it is relatively insensitive to photolysis or to natural hydrolysis.

Although TBP is not toxic to the human organism, it is nonetheless toxic with respect to various aquatic organisms (trout, shrimp, algae, bacteria), which can result in an ecological imbalance at the contaminated sites.

Documents exist that disclose general methods of degrading organic compounds in liquid effluents:

U.S. Pat. No. 6,472,198 discloses the degradation of chlorinated organic compounds using indigenous bacteria, in particular of methanogenic or acetogenic type, or bacteria responsible for the dehalogenation or denitrification, these bacteria functioning under conditions of aerobiosis or anaerobiosis. Such a method is not suitable for the degradation of TBP.

U.S. Pat. No. 6,106,719, discloses the use, for the treatment of liquid waste containing both organic compounds and inorganic compounds containing nitrogen or phosphorus, of a combination of bacteria in the form of solid granules, under conditions of anaerobiosis and in the presence of light; said combination of bacteria comprises (a) a mixture of non-photosynthetic bacteria: acid fermentation bacteria and/or methane-producing bacteria, and (b) a mixture of photosynthetic bacteria (purple non-sulfur bacteria, purple sulfur bacteria and green sulfur bacteria, such as *Chrorobium limicola, Chromatium vinosum, Rhodopseudomonas palustris* or *Rhodobacter capsulatus*). Such a treatment makes it possible to digest the organic material, and to digest the inorganic compounds comprising nitrogen and/or phosphorus. In the method disclosed in that patent, the disappearance of the inorganic phosphorus is linked to the growth of the photosynthetic bacteria. Such a method is not therefore suitable for the treatment of TBP.

U.S. Pat. Nos. 6,416,993 and 6,465,240 disclose a method of degrading liquid organic and inorganic waste, which comprises two steps of treatment with photosynthetic microorganisms: a first treatment with one or more photosynthetic prokaryote(s) and, preferably, a consortium of photosynthetic bacteria (purple non-sulfur bacteria: *Rhodospirillum, Rhodopseudomonas, Rhodobacter, Chromatium, Rubrivivax* or cyanobacteria), and then a second treatment with photosynthetic algae. More specifically, said method disclosed makes it possible to treat waste containing high concentrations of total organic carbon (TOC), of biochemical oxygen demand (BOD), of nitrogen (including aqueous ammonia) and of phosphorus (P, including phosphates, polyphosphates, organic phosphates) and also other organic or inorganic substances. However, these methods are not suitable for the degradation of TBP, which may be present at high concentrations (of the order of 100 mg/ml); in fact, the methods disclosed in those two patents apply to the treatment of agricultural effluents, such as liquid manure, in which little or no TBP is found. In addition, TBP is reputed to be toxic for bacteria and algae at low concentrations (Nakamura A., 1991, *International Program on Chemical Safety-Environmental Health Critiria* 112-*Tri-n-Butyl Phosphate QV* 627. World Health Organisation).

The methods of the prior art that are aimed at the treatment of all organic and inorganic products are not therefore suitable for the treatment of waste comprising TBP, since the growth of the algae and of the nonphotosynthetic bacteria used is generally inhibited by TBP.

The degradation of TBP by microorganisms has been the subject of few studies; it generally uses microorganisms that act under conditions of aerobiosis:

U.S. Pat. No. 5,453,375 discloses a method of degrading TBP which uses the bacterial strain *Acinetobacter* sp., under conditions of aerobiosis.

In other studies, the team of R. A. Thomas et al. [1, 2, 3, 4] has disclosed the use of a mixture of microorganisms of the genus *Pseudomonas* spp., for degrading TBP under conditions of aerobiosis.

In the article by S. Owen et al. [5], the use of *Citrobacter* sp. bacteria is recommended under conditions of aerobiosis for degrading TBP.

The conditions (aerobiosis) disclosed in those documents have the following drawbacks:
  low TBP degradation yield,
  random method reproducibility.

Consequently, all the methods of treating organic waste recommended in the prior art are therefore unsuitable for the treatment of TBP, insofar as none of them discloses a method that is at the same time stable, reproducible, effective and high-yield (>400 mg/l) for degrading TBP, present in varying concentration ranges.

Consequently, the Applicant has given itself the aim of providing a method of treating liquid waste containing TBP, which better satisfies the practical needs than the methods of the prior art, in particular in that it effectively makes it possible to degrade TBP, with a good yield and in particular, under certain conditions, a yield greater than 400 mg/l, while at the same time being reproducible.

SUMMARY OF THE INVENTION

A subject of the present invention is a method of treating or purifying liquid waste loaded with TBP, characterized in that it comprises the steps consisting in:

(1) bringing said liquid waste into contact with at least one TBP-resistant purple non-sulfur photosynthetic bacterial strain selected from the group consisting of *Rhodopseudomonas palustris* (*Rp. palustris*), *Rhodospirillum rubrum* (*Rs. rubrum*), *Rhodobacter capsulatus* (*Rb. capsulatus*) or *Rhodobacter sphaeroides* (*Rb. sphaeroides*)

and also said bacterial strains that have been modified so as to overexpress cytochrome P450, under conditions that allow the degradation of the TBP present in said waste, whatever the initial concentration of TBP; and (2) recovering the purified liquid effluents.

In accordance with the invention, for optimal degradation, a carbon source, either endogenous or exogenous, is necessary.

According to an advantageous embodiment of the method according to the invention, step (1) is carried out under conditions of anaerobiosis or microanaerobiosis.

In general, according to the oxygen demands, various conditions: aerobiosis, microanaerobiosis (or microaerobiosis or microaerophilia) and strict anaerobiosis, are defined in the following way:

aerobiosis: an aerobic microorganism is a microorganism that can use oxygen as a final electron-acceptor;

microanaerobiosis or microaerobiosis: a microorganism capable of developing under conditions of "microaerobiosis" or "microanaerobiosis" is a microorganism that is incapable of growing when the oxygen concentrations reach those encountered in air (20%) but is nevertheless capable of growing in the presence of low amounts of oxygen (2 to 10%) such microorganisms exhibit better growth conditions in the presence of small amounts of free oxygen; in particular, they develop under the surface in a tube, at the level where the oxygen concentrations are optimal for their growth (*Microbiology. Principles and Applications,* 1996, 3rd Edition, Black J G, Prentice Hall, Upper Saddle River, N.J., pages 144-148);

strict anaerobiosis: an anaerobic microorganism is only capable of developing in the absence of molecular oxygen.

For the purpose of the present invention, the term "anaerobiosis", applied to non-sulfur photosynthetic bacteria, is equivalent to the term "microaerophilia" or "microanaerobiosis", more commonly used for these bacteria; a bacterium is said to be microaerophilic when it requires only a low oxygen concentration (from 2 to 10%) for its growth; this term is also used to indicate that the bacteria concerned have a metabolic activity under aerobic conditions, but grow better under non-strict anaerobic conditions ($[O_2]>5\,\mu M$ and $<70\,\mu M$) (*Biology of Microorganisms,* 9th Edition, 2000, M T Madigan, J M Martinko et J Parker, Prentice Hall, Upper Saddle River, N.J., pages 158-162). As regards the purple non-sulfur photosynthetic bacteria, the anaerobiosis (or microaerophilia or microanaerobiosis or microaerobiosis) can be obtained even in the presence of light (natural light or artificial light, such as an incandescent lamp having an emission spectrum of between 350 and 1100 nm) and an energy within a range of 1 to 2000 µmol of photons/m$^2$/s and in a medium that has undergone a degassing cycle so as to obtain a residual oxygen concentration of between 5 µM and 70 µM, or in the absence of light, but in the presence of an electron-acceptor commonly used for photosynthetic bacteria, such as trimethylamine-N-oxide (TMAO), nitrates and dimethyl sulfoxide (DMSO).

In general, in the settling tanks used, the purple non-sulfur bacteria used are preferably at the bottom of said tank ($O_2$ percentage of the order of 2 to 10%).

According to another advantageous embodiment of the invention, said TBP-resistant bacterial strain used in step (1) of the method is preferably selected from the group consisting of *Rp. palustris* and *Rs. rubrum*, which have an ability to degrade TBP that is greater than 400 mg/l, and preferably greater than 426 mg/l. As regards *Rp. palustris*, the strains devoid of endogenous plasmid are also included in the invention; such strains are hereinafter referred to as ΔpRpa1 strains.

According to another advantageous embodiment of the method according to the invention, step (1) comprises the use of a mixture of TBP-resistant purple non-sulfur bacterial strains comprising at least one strain selected from the group consisting of *Rhodospirillum rubrum* (*Rs. Rubrum*) and *Rhodopseudomonas palustris* (*Rp. palustris*) and at least one other strain selected from the group consisting of *Rhodobacter capsulatus* (*Rb. capsulatus*) and *Rhodobacter sphaeroides* (*Rb. sphaeroides*).

In accordance with the invention, the TBP-resistant purple non-sulfur bacterial strains are preferably selected from the strains *Rp. palustris* CGA009 No. ATCC BAA-98, No. ATCC 17002, No. ATCC 17007, No. DSM 8283, No. DSM 126, No. DSM 7375, No. DSM 131, No. DSM 25, No. DSM 124 and No. DSM 130, the strain *Rs. rubrum* S1 No. ATCC 11170, the strain *Rb. capsulatus* Saint-Louis No. ATCC 23782 and the strain *Rb. sphaeroides* 2.4.1. No. ATCC 17023.

Surprisingly, the inventors have selected TBP-resistant purple non-sulfur bacterial strains that make it possible to obtain high degradation yields, whatever the initial concentration of TBP, and in a single-step purification method; the method according to the invention is effective and reproducible for purifying and depolluting the environment, and in particular degrading the TBP in liquid waste, due to the use, preferably under conditions of microanaerobiosis, of one or more pure TBP-resistant purple non-sulfur bacterial strains, which, alone or as a mixture, make it possible to obtain a TBP degradation at least equal to 53 mg/l, and preferably greater than 400 mg/l of liquid effluents.

The term "liquid waste" is intended to denote polluted effluents and/or aquatic sites. This liquid waste contains TBP to be degraded, but may also contain other organic and inorganic compounds. They originate from industry, and in particular from the nuclear industry.

For the purpose of the present invention, the term "TBP-resistant purple non-sulfur bacterial strain" is intended to mean a strain whose growth is not inhibited in the presence of TBP concentrations that are at least within the TBP concentration range of 12-37 µM (Nakamura, mentioned above) and, of course, also at higher concentrations of TBP.

According to yet another advantageous embodiment of said method, step (1) is carried out at a temperature of between 10° C. and 37° C., preferably at 30° C., at a pH of between 5.5 and 8.5, preferably at 6.9, and for at least 15 days, preferably between 15 and 21 days.

In accordance with the invention, step (1) is preferably carried out in a settling tank.

The incubation period or contact period must be sufficient for the bacterial strain or the mixture of bacterial strains to be able to grow exponentially, so as to allow degradation of the TBP with a high yield. This incubation period is preferably between several days and several weeks, according to the incubation temperature used; for example, an incubation period of 21 days at a temperature of 30° C. makes it possible to obtain a yield of greater than 400 mg/l.

According to another advantageous embodiment of said method, the amount of TBP in said liquid waste before treatment is between 0.01 mM and 1 M; this range of values is sufficiently broad to correspond to the conditions usually encountered in cases of pollution; specifically, the readings taken under conditions of pollution give TBP waste values of the order of 100 mg/l, i.e. 0.375 mM. Consequently, it is not generally necessary to dilute or concentrate the sample to be treated before it is brought into contact with the bacterial inoculum. In addition, within this range of values, the degradation yield is particularly high. Specifically, the method according to the invention allows the degradation of TBP concentrations of the order of 0.1 to 2 mM; no inhibition of bacterial growth having been observed at these concentrations. In particular, when the initial TBP concentration is greater than 1 mM, complete degradation of the TBP is obtained under the conditions of the invention. More specifically, using the method according to the present invention, it is possible to obtain, after 3 weeks in incubation, TBP degradation yields of between 1 and 1000 mg per liter of medium; the highest value corresponding to the theoretical maximum solubility of TBP in water at 25° C.

In order to be able to obtain an effective and reproducible method with high TBP degradation yields according to the invention, a pure strain or a mixture of TBP-resistant purple non-sulfur photosynthetic bacteria should be inoculated. According to the invention, it is preferable to use a pure strain of photosynthetic bacteria, with the aim of optimizing the treatment conditions and thus the TBP degradation yield.

According to another advantageous embodiment of the invention, the amounts of bacteria inoculated into the medium to be treated in step (1) are advantageously between $10^4$ and $10^{10}$ bacteria per ml of medium to be treated. However, they depend on the general conditions used (temperature, luminosity, etc.). Consequently, in general, the term "sufficient amount" of bacteria to be inoculated is intended to mean the seeding concentration, i.e. the initial number of bacteria, making it possible, by exponential growth, and under appropriate conditions, to achieve a sufficient biomass to observe TBP degradation.

The TBP-resistant photosynthetic bacterial strains as used in the present invention have the advantage of providing good TBP biodegradation yields even after having been subjected to a subsequent treatment (large number of subcultures, for example).

According to another advantageous embodiment of the method according to the invention, when the endogenous carbon source is not sufficient, an additional carbon source is added, in step (1), to the medium to be treated; this additional carbon source is advantageously a buffered solution containing a yeast extract at a concentration of between 0.1 and 10 g/l (preferably at 1 g/l), or one of the following organic salts: succinate, glutamate, benzoate, malate or fumarate at a concentration of between 2 and 20 mM (preferably at 10 mM), and growth factors, including at least biotin and para-aminobenzoic acid each at a concentration of between 2 and 40 µg/l.

Prior to said bringing into contact according to step (1), the TBP-resistant purple non-sulfur bacteria are selected by culturing on medium containing at least 12 µM, and preferably at least 1 mM of TBP, and are then cultured according to methods known to those skilled in the art, for instance those described in *Bergey's manual of systematic bacteriology*; Williams & Wilkins Edition or in "*The photosynthetic bacteria*" R. K. Clayton and W. R. Sistrom; Plenum Press.

In the context of the invention, the method is advantageously carried out by non-aerated lagooning.

The term "non-aerated lagooning" is intended to mean a device comprising at least one settling tank with a depth ranging from 0.5 to 1 meter for a surface area in accordance with the effluent flow rate, given that the retention time must be at least 15-21 days under optimal temperature and lighting conditions. The subsequent separation of the bacteria and the treated medium is promoted by the conditions used (microanaerobiosis, settling tank).

When the bacterial growth has reached substantial value, and before releasing the purified effluents into the environment, it may be useful to recover the bacteria by filtration (using a diatom filter, for example) or by continuous centrifugation, before reinjecting them into the system.

A subject of the present invention is also a method of following or monitoring the degradation of TBP in liquid waste, which method comprises:
- carrying out the method of treating liquid waste loaded with TBP, as defined above, and then
- taking a sample of treated medium at least at time t+15 days and measuring, in said sample taken, the concentration of residual TBP; this measurement can be carried out manually or automated when there is a large number of samples to be analyzed. The step for measuring the residual TBP (that has not been degraded by the bacteria) can be carried out by any known technique in analytical chemistry commonly used, and more particularly in the field of organophosphorus compounds. For a reliable and accurate measurement, a chromatographic technique is generally used, and more specifically high performance liquid chromatography coupled with refractometry. The entire process can be automated.

A subject of the present invention is also a boxed set for carrying out the method of treatment according to the invention, characterized in that it comprises at least one TBP-resistant purple non-sulfur photosynthetic bacterial strain chosen from the group consisting of *Rp. palustris, Rs. rubrum, Rb. capsulatus* or *Rb. sphaeroides*, and also said bacterial strains modified so as to overexpress cytochrome P450, as defined above. The mixture of strains preferably comprises at least the *Rp. palustris* strain or the *Rs. rubrum* strain, as specified above. As regards *Rp. palustris*, also included in the context of the invention are the strains devoid of endogenous plasmid; such strains are hereinafter referred to as ΔpRpa1 strains.

A subject of the present invention is also purple non-sulfur photosynthetic bacterial strains, characterized in that they are TBP-resistant, in that they are selected from the group consisting of *Rp. palustris, Rs. rubrum, Rb. capsulatus* or *Rb. sphaeroides*, and in that their DNA includes at least one additional copy of the gene encoding a homologous cytochrome P450.

Such strains comprising at least one additional copy of a homologous gene encoding a cytochrome P450 allow overexpression of said cytochrome P450.

According to an advantageous embodiment of said strains, they consist of an *Rp. palustris* CGA009 strain comprising a gene encoding *Rp. palustris* cytochrome P450, under the control of the LHαβ$_e$ promoter, described in M. H. Tadros et al. (10) (*Rp. palustris* LH5939 strain). The gene encoding *Rp. palustris* cytochrome P450 is in particular described in the Oak Ridge National Laboratory (ORNL) database under the gene No. 5939 (site: http://genome.ornl.gov) or under the Genbank access No. NZ_AAAF01000001.1.

A subject of the present invention is also a device for purifying liquid waste loaded with TBP by carrying out the degradation method as described above, characterized in that it comprises at least one settling tank suitable for bringing the purple non-sulfur bacteria into contact with the medium to be treated, preferably under conditions of microanaerobiosis. Such a device uses in particular the non-aerated lagooning technique, which consists in passing the polluted effluents, loaded with TBP, through a series of tanks in the open air, the first of which, called a settling tank, is specifically inoculated, in the context of the invention, with TBP-resistant purple non-sulfur photosynthetic bacteria. In this case, the microanaerobiosis takes place at the bottom of the head tank, where the sludge is deposited. Said settling tank preferably has a depth ranging from 0.5 to 1 meter for a surface area in accordance with the effluent flow rate, given that the retention time must be at least 15-21 days under the optimal temperature and lighting conditions as defined above.

According to an advantageous embodiment of said device, it comprises, in addition to said settling tank, means for introducing said liquid waste containing TBP into said settling tank, means for introducing the bacterial inoculum, means for draining the TBP-purified effluents off to the outside, and also means for recovering the bacteria to be recycled.

According to another advantageous embodiment of said device, said means for recovering the bacteria is advantageously selected from the group consisting of diatom filters and continuous centrifuges.

Besides the provisions above, the invention also comprises other provisions that will emerge from the following description, which refers to examples of implementation of the invention and also to the attached drawings, in which:

BRIEF DESCRIPTION OF THE DRAWINGS

In FIG. 2A, the scale of the left-hand y-axis corresponds to the optical density of the culture measured at 660 nm. The scale of the right-hand y-axis corresponds to the TBP concentration (continuous line, (■)). Under conditions of aerobiosis, the degradation curve can be plotted by means of the function $a.e^{tln2/t^{1/2}}+b$ with a=28, b=0.55 and $t^{1/2}$=~0.1 day. Under conditions of microanaerobiosis, the curve can be plotted by means of the function $a_1.e^{tln2/t1}+a2.e^{tln2/t2}$ with $a_1$=23, $a_2$=77 and $t_1$=13.5 days. These scales of FIG. 2B are identical to those of FIG. 2A;

Figure 1:
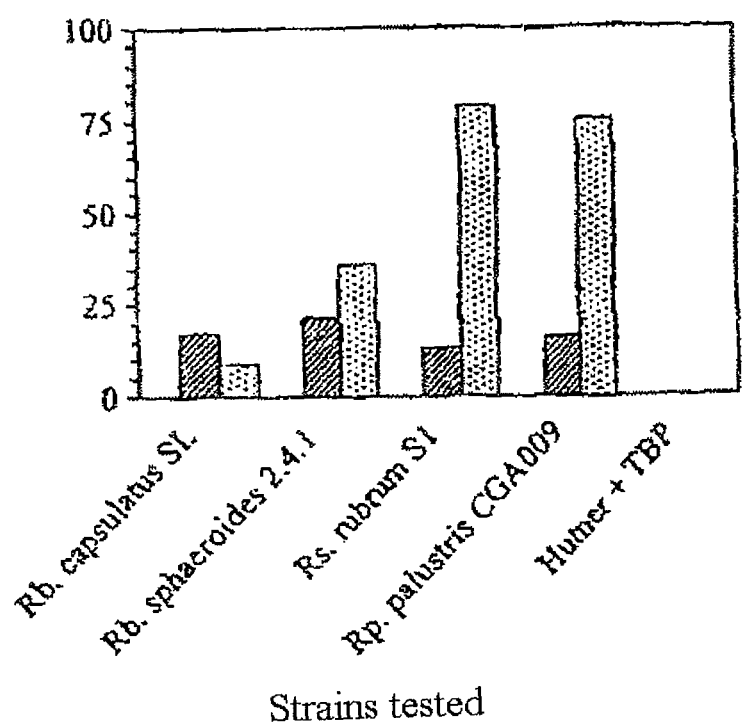
FIG. 1 represents the consumption of TBP (expressed as a percentage) under conditions of aerobiosis (hatched bars) and under conditions of anaerobiosis (bars with dots) for each of the purple non-sulfur photosynthetic bacterial strains tested (*Rb. capsulatus* Saint-Louis (ATCC 23782), *Rb. sphaeroides* 2.4.1 (ATCC 17023), *Rs. rubrum* S.1. (ATCC 11170), and *Rp. palustris* CGA009 (ATCC BAA-98)). Noninoculated Hutner culture medium is used as a control.

It should be understood, however, that these examples are given only by way of illustration of the subject of the invention, of which they in no way constitute a limitation.

DETAILED DESCRIPTION OF THE INVENTION

Example 1

Comparison of the TBP Degradation Yield Under Conditions of Aerobiosis and Anaerobiosis (Microanaerobiosis or Microaerophilia) by Various Purple Non-Sulfur Photosynthetic Bacteria A. Materials and Methods During this experiment, the concentration of residual TBP under conditions of aerobiosis and under conditions of microanaerobiosis, after 3 weeks of culture with the following photosynthetic bacteria is measured: *Rb. capsulatus* Saint-Louis (ATCC 23782), *Rb. sphaeroides* 2.4.1 (ATCC 17023), *Rs. rubrum* S.1. (ATCC 11170) and *Rp. palustris* CGA009 (ATCC BAA-98).

The photosynthetic bacteria are incubated in a Hutner medium [6] in which the pH is between 6.5 and 7.5, in the presence of 2 mM of TBP, either under conditions of aerobiosis or under conditions of microanaerobiosis. Under conditions of aerobiosis, the bacteria are incubated in the dark at a temperature of 30° C., the culture medium being subjected to shaking (150 rpm).

Under conditions of microanaerobiosis, the bacteria are incubated under light (incandescent lamp having an emission spectrum of between 400 and 900 nm) at 30° C. The microanaerobiosis is obtained by degassing the medium before inoculation, by placing the flask under a negative pressure using a vacuum pump, so as to attain a low oxygen tension of the order of 70 µM.

The media are sterilized by autoclaving at 120° C. for 15 minutes. The TBP is added, after sterilization, to a final concentration of 2 mM, which is below the saturation point of the product of solubility of TBP in water, which is less than 1 g/l (3.7 mM) at 25° C.

The growth is monitored with a spectrophotometer at an optical density (OD) at 660 nm and the samples are taken regularly and stored at −20° C. for the subsequent measurements of residual TBP.

The culture is centrifuged at 5000 g for 10 minutes in order to separate the bacteria from the culture medium. The supernatant is then recovered, and the residual TBP concentration is determined thereon. An equal volume of dichloroethane and of tripropyl phosphate (TPP) is added to the aqueous supernatant. The solvent makes it possible to extract the TBP and the other hydrophobic organic compounds, and the TPP is used as an internal standard for quantifying the extraction efficiency and for calibrating the results during the subsequent analyses by high performance liquid chromatography (HPLC). The samples are mixed by vortexing for 1 minute and are then left to stand for 30 minutes. In order to remove all traces of water, the organic phase (lower phase) is then filtered on a phase separator (IPS, Whatman) followed by evaporation overnight at 30° C. or, alternatively, a slight stream of nitrogen is passed through at ambient temperature for 15 minutes. The samples are diluted in dodecane for subsequent HPLC analysis.

Measurements are then carried out by HPLC analyses using a Brownlee Spheri-5 amino column (Perkin Elmer) integrated into a Waters 1525 model HPLC. Elution is carried out using a mixture of heptane and ethyl acetate (75/25, vol/vol) with a flow rate of 1 ml/min as described in European patent 0 578 579. The TBP is measured using a Waters 2414-type refractometer and the chromatography profiles are analyzed using the Breeze program (sold by the company Waters). The TBP concentration is defined by the ratio between the areas of the peaks of the TBP and TPP compounds.

The TBP and TPP compounds, the purity of which is estimated to be greater than 99%, and all the chemical products mentioned above which are used for extracting the TBP and during the HPLC analysis are provided by Sigma-Aldrich.

B. Results

The results are given in FIG. 1.

Under conditions of aerobiosis, the TBP degradation yields reach 13 to 22% after incubation for 21 days. These values are similar to those obtained with natural isolates such as the *Serratia odorifera* sp. strain.

Under photosynthetic conditions (microanaerobiosis), the degradation yield is clearly improved in certain strains, reaching almost 80% for *Rp. palustris* and *Rs. rubrum* after 3 weeks of culture. This yield is reproducible, whatever the subsequent treatment to which said strains are subjected.

Example 2

Growth of the *Rp. palustris* CGA009 Strain and Kinetics of Degradation of TBP by the Same Strain Either Under Conditions of Aerobiosis, or Under Conditions of Microanaerobiosis, or Under Conditions of Anaerobiosis Because of the results obtained in Example 1, the *Rp. palustris* strain was more particularly studied.

A. Materials and Methods

Strains and Media

The strains and the media used are given in Table I below.

TABLE I

Description of the various plasmids and strains used:

| Strain or plasmid | Characteristics[a] | Source or reference |
|---|---|---|
| *E. coli* strains | | |
| DH5α phe | F⁻ Φ80dlacZΔM15Δ(lacZYA-argF)U169 recA1 endA1 hsdR17 ($r_K^- m_K^+$) sup E44 λ⁻gyrA thi-1 relA1 phe::Tn10dCm | (8) |
| HB101 | F⁻ Δ(gpt-proA)62 leuB6 supE44 ara-14 glaK2 lacYI Δ(mcrC-mrr) rpsL20 (St$^r$) xyl-5 mtl-1 recA13 | (7) |
| *Rp. palustris* strains | | |
| wt | CGA009 strain, genome completely sequenced | see above-mentioned site |
| ΩLH5939 | 5939 Ω with plasmid pCB07 | Invention |
| ΔpRpa1 | Derived from the strain CGA009; comprises no endogenous plasmid | Invention |
| Plasmids | | |
| pGEM-T ® | Cloning vector, Ap$^r$ | Promega |
| pBBR1MCS2 | Cloning vector, Km$^r$ | (9) |
| pCB04 | pGEM-T ® with a 374 pb fragment of the LHαβ$_e$ promoter Ap$^r$ | Invention |
| pCB06 | HindIII + SacI fragment of the 5939 gene amplified by PCR and cloned into pBBR1MCS2 | Invention |
| pCB07 | KpnI + HindIII fragment of pCB04 cloned into pCB06, Km$^r$ | Invention |
| pMG105 | Cloning vector, Km$^r$ | (11) |
| pRpa1 | Endogenous, from *Rp. palustris* CGA009 | (12) |

[a]Ap, ampicillin; Km, kanamycin

*Rp. palustris* was cultured in Hutner medium (6) or in a PM medium: 12.5 mM $Na_2HPO_4$; 12.5 mM $KH_2PO_4$; 7.5 mM $(NH_4)_2SO_4$; 0.1 mM $Na_2S_2O_3.5H_2O$; 14.5 mM of p-aminobenzoic acid; 0.85 µM EDTA; 3.8 nM $ZnSO_4.7H_2O$; 2.5 nM $FeSO_4.7H_2O$; 0.9 nM $MnSO_4.7H_2O$; 0.16 µM $CuSO_4.7H_2O$; 86 nM $Co(NO_3)_2.6H_2O$; 46 nM $Na_2B_4O_7.10H_2O$; 0.1 mM of nitrilotriacetic acid; 0.24 mM anhydrous $MgSO_4$; 45 µM $CaCl_2$; 15 nM $(NH_4)_6Mo_7O_{24}.4H_2O$.

The media were sterilized by autoclaving at 120° C. for 15 minutes. A source of carbon (sterile succinic acid) and of $Na_2CO_3$ (only under photosynthetic conditions) were each added to the PM medium at a final concentration of 10 mM.

To culture these bacteria on dishes of PM medium, a 2× agar-agar solution (34 g·l⁻¹) was mixed, after autoclaving, with 2×PM medium.

For the photosynthetic growth conditions, the dishes were incubated at 30° C., in a GENbag Anaer (Biomerieux, France), with exposure to light.

When TBP was required, it was added directly to the culture medium, after sterilization, at a final concentration of 2 mM (the solubility of TBP in water is approximately 2.5 mM). The culture conditions were either those for aerobiosis (30° C., in the dark, with shaking at 300 rpm) or photosynthetic conditions (30° C., light, 75 µmol of photons·m$^{-2}$·s$^{-1}$). Two types of photosynthetic conditions were used in accordance with the $O_2$ concentration:
(1) Microanaerobiosis was obtained by simple degassing of the medium. The residual $O_2$ concentration was approximately 70 µM, as measured with a Clark electrode.
(2) Anaerobiosis was obtained by subjecting the medium to 5 degassing cycles followed by a step consisting in sparging with argon sufficient to obtain an oxygen concentration of less than 5 µM.

The growth was monitored by means of the optical density at 660 nm ($OD_{660}$). For $OD_{660}$ values≥0.8, the samples were diluted so as to allow an accurate measurement. Samples were taken periodically and stored at −20° C. for other TBP tests.

Preparation of Samples for Assaying TBP

The cultures were centrifuged to remove the bacteria (10 minutes at 5000 g) and the supernatant was used to determine the residual TBP concentration. For the cell extracts, the TBP assays were carried out directly on the protein mixture. Triphosphyl phosphate (TPP) was used as an internal standard for quantifying the extraction efficiency and for calibrating the results for the subsequent high performance liquid chromatography (HPLC) analysis. The TBP was extracted from the aqueous system by adding an equivalent volume of dichloroethane+2 mM TPP to the aqueous supernatants. The samples were vigorously mixed on a vortex for one minute. After 30 minutes without agitation, the organic phase (lower phase) was filtered on a phase separator (IPS, Whatman), so as to remove all traces of the aqueous phase, and evaporated over night at 30° C. The dried samples were then diluted in dodecane for the HPLC analysis.

HPLC Analysis

The HPLC analyses were carried out using a Spheri-5 amino column (Perkin Elmer) connected to a Waters 1525 model HPLC, as specified in Example 1. For the elution, a mixture of heptane and ethyl acetate (75/25, v/v) was used at a flow rate of 1 ml·min$^{-1}$ as described in European patent 0 578 579. The TBP and the TPP were detected by refractometry (Waters Refractometer 2414) and the refraction chromatography profiles were analyzed using the Waters Breeze Software. The TBP concentration was estimated from the ratio of the areas of the peaks for TBP and for TPP. Under these conditions, the TBP detection threshold was approximately 5 µM (see also Example 1).

Enzyme Assays

The crude extracts and the fractionated proteins were used for the TBP degradation studies. As a control, sterile buffer containing 2 mM of TBP, boiled (10 minutes at 95° C.) crude extracts and crude extracts of *E. coli* DH5α were tested in order to estimate the abiotic disappearance of TBP. The crude extracts were dialyzed with the Ultrafree Biomax 10 000 D system (Millipore) so as to decrease the concentration of small molecules. $FADH_2$ and $FMNH_2$ were obtained by reduction of a solution of FMN and of FAD with a small excess of sodium dithionite. All the cofactors used were added to the cell extracts at a final concentration of 10 µM.

The assays were carried out by testing the degradation of TBP by proteins in 1 ml of 400 mM Tris-HCl, pH 6.5, at 40° C. The temperature and pH optimums were determined. The residual TBP was assayed by HPLC.

B. Results

Figure 2:
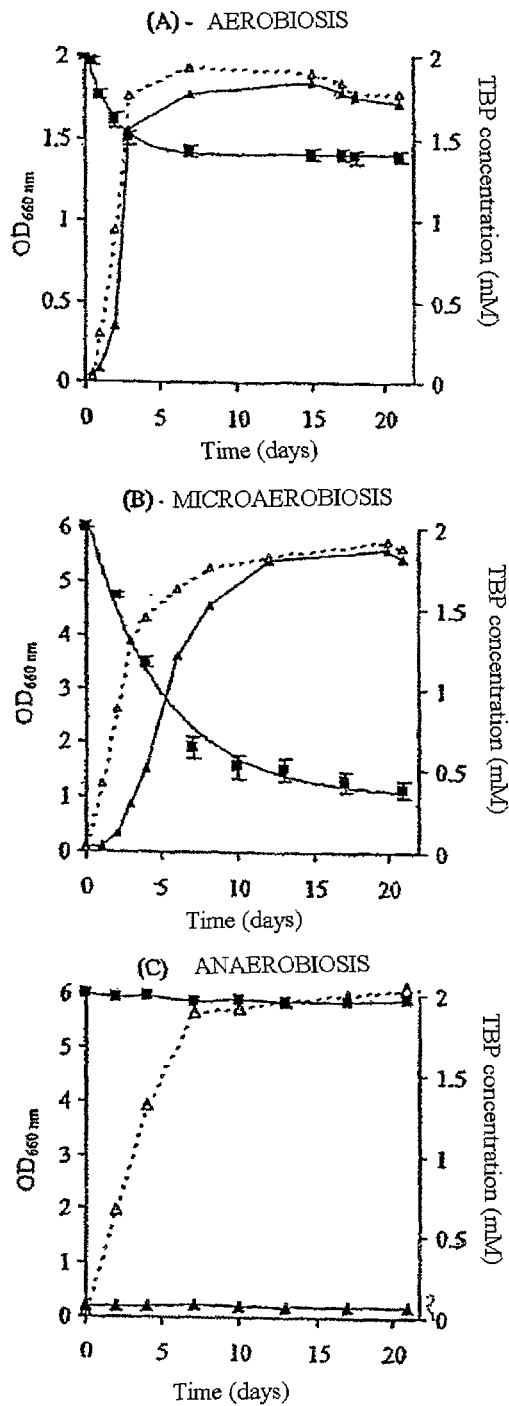
FIG. 2 represents the growth of the *Rp. palustris* CGA009 strain (ATCC BAA-98) under aerobic (A), photosynthetic (microanaerobic) (B) and anaerobic (C) conditions in Hutner culture medium, in the presence (continuous line, (▲)) and in the absence (discontinuous line, (Δ)) of 2 mM TBP during bacterial growth.

The results are given in FIG. 2.

The growth of the *Rp. palustris* strain in the presence of TBP (2 mM) or in the absence of TBP was measured. Both under conditions of aerobiosis (FIG. 2A) and under conditions of microanaerobiosis (FIG. 2B), the growth of the strain begins after a lag period, this being shorter under conditions of aerobiosis, and the growth kinetics then accelerate so as to reach those of the control (absence of TBP). Under conditions of aerobiosis, the degradation kinetics are monophasic; they can be reflected by an exponential curve with a $t_{1/2}$ of 1.1 days (amplitude 28%). The initial TBP consumption rate is 13 µmol/l/h (FIG. 2A).

Under conditions of microanaerobiosis, the growth kinetics are biphasic; they can be reflected by a series of two exponential curves with a $t_{1/2}$ of 0.94 day (amplitude 23%) and a $t_{1/2}$ of 13.5 days (amplitude 77%). The initial TBP consumption rate is 15 µmol/l/h (FIG. 2B).

These results demonstrate the existence of two different mechanisms: a rapid mechanism that operates under conditions of aerobiosis and of microanaerobiosis, and another, slower mechanism that operates only under conditions of microanaerobiosis. It should be noted that, under the two culture conditions, the rapid phases correspond virtually to the same exponential curve, suggesting the occurrence of two similar mechanisms independent of the culture conditions, whereas the slow phase appears to be associated with microanaerobiosis. It is notable that, under conditions of microanaerobiosis, the rapid TBP degradation phase appears concomitantly during the growth lag mentioned above, whereas the clear acceleration in growth of the strain is accompanied by a slowing of the TBP degradation kinetics.

Moreover, under conditions of strict anaerobiosis, no growth is observed in the presence of 2 mM TBP, whereas, in the absence of TBP, growth of the same type as that observed under the conditions of microanaerobiosis is observed (FIG. 2C).

Example 3

Effect of various Concentrations of TBP on the Growth of the *Rp. palustris* CGA009 Strain and the Kinetics of Degradation of TBP by the Same Strain Under Conditions of Microanaerobiosis A. Materials and Methods The culture conditions and the TBP analysis conditions are identical to those used in Example 2.

B. Results

Figure 3:
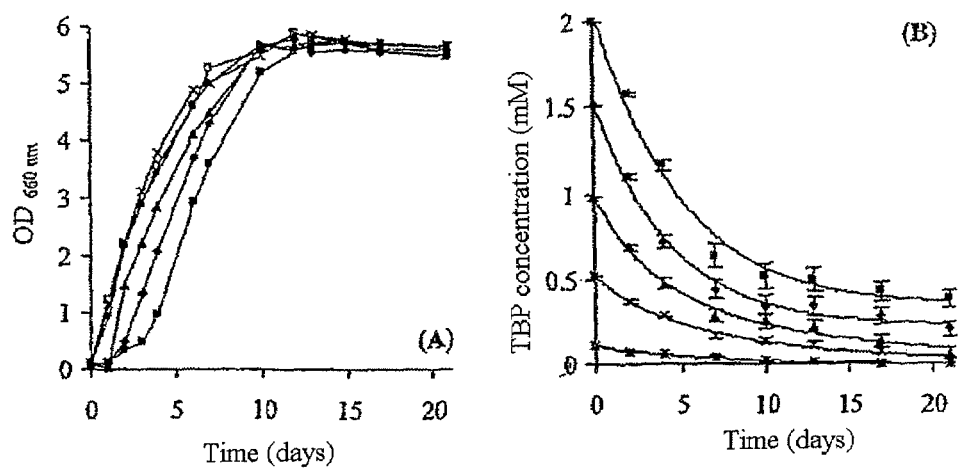
FIGS. 3A and 3B represent, respectively, the growth of the *Rp. palustris* CGA009 strain (ATCC BAA-98) under photosynthetic conditions (microanaerobiosis) in Hutner culture medium in the presence of various concentrations of TBP, and a kinetic study of TBP consumption for the *Rp. palustris* CGA009 strain (ATCC BAA-98) under the same conditions. The scales of FIG. 3A are identical to those of FIG. 2. That of FIG. 3B corresponds to the initial concentration of TBP expressed in mM. The TBP concentrations are 0 mM (asterisks), 0.1 mM (crosses), 0.5 mM (triangles), 1 mM (circles), 1.5 mM (diamonds) and 2 mM (squares)

The results are illustrated in FIG. 3.

The *Rp. palustris* CGA009 strain was cultured in the presence of varied concentrations of TBP: 2, 1.5, 1, 0.5 and 0.1 mM under conditions of microanaerobiosis.

According to these results, a shortening of the growth lag is noted when the TBP concentration is reduced. In addition, at a concentration of less than 1 mM, the growth of the strain is similar to that observed in the medium lacking TBP (FIG. 3A). The TBP degradation yields improve when the TBP concentration is less than 1 mM; the TBP is then almost entirely degraded in 21 days (FIG. 3B).

No inhibition of the TBP degradation by a secondary metabolite is observed with the *Rp. palustris* CGA009 strain, under conditions of microanaerobiosis.

13

Example 4

Role of Cytochrome P450 by Studying the Effect of a Cytochrome P450 Inhibitor, Carbon Monoxide (CO), on the Growth of the *Rp. palustris* Strain in the Presence or Absence of TBP In order to demonstrate that one or more cytochrome(s) contribute actively to the degradation of TBP by the *Rp. palustris* CGA009 strain, this bacterial strain is incubated in the presence of carbon monoxide (CO), which is a cytochrome P450 inhibitor, in the presence (2 mM) or absence of TBP. It is possible to carry out the CO treatment, prior to inoculation of the culture, in two different ways: either by mild bubbling, or by the addition of a culture medium already saturated with CO.

An *S. odorifera* strain, which can only grow under aerobic conditions in a Tryptic soy broth medium (Tsb; Sigma-Aldrich), is used by way of comparison, this strain being capable of degrading TBP, but with a lower overall yield.

The culture conditions and conditions for measuring TBP are identical to those used in Example 2.

The results are illustrated in FIG. 4.

Figure 4A:
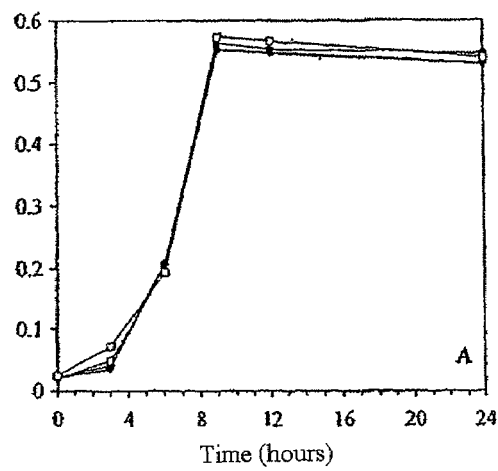
FIG. 4A represents the growth of *Serratia odorifera* sp. in Tsb medium under conditions of aerobiosis, in the presence (circles) and in the absence (squares) of carbon monoxide in the culture medium.
Figure 4B:
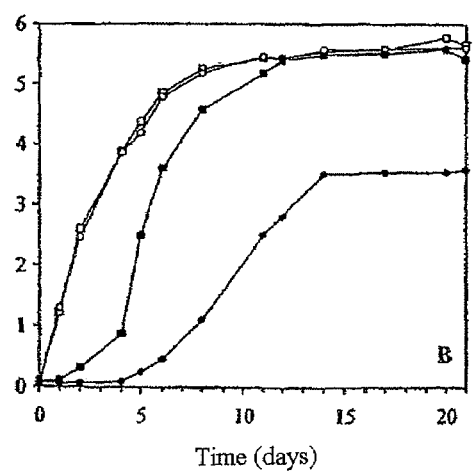
FIG. 4B represents the growth of the *Rp. palustris* CGA009 strain (ATCC BAA-98), expressed in units of optical density at 660 nm, under photosynthetic conditions in Hutner culture medium in the presence (circles) and in the absence (squares) of carbon monoxide in the culture medium. All the bacteria are incubated in the presence (full symbols) and in the absence (empty symbols) of 2 mM TBP.
Figure 5:
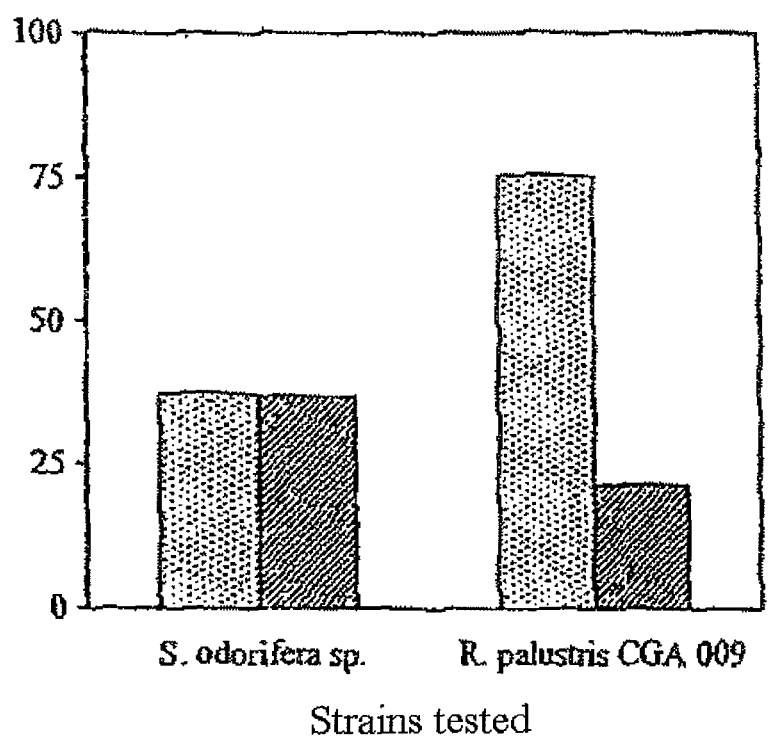
FIG. 5 represents the TBP consumption, expressed as percentage of residual TBP, by the *Serratia odorifera* sp. strain and the *Rp. palustris* CGA009 strain (ATCC BAA-98) after 24 hours and 3 weeks, respectively, in the absence (dotted bars) and in the presence (hatched bars) of carbon monoxide in the culture medium.

As shown in FIGS. 4A and 4B, respectively, the presence of CO in the medium does not affect the growth of either of the two strains when TBP is absent from the medium, nor does it affect the growth of the *S. odorifera* strain when the latter is placed in the presence of TBP. In addition, the growth of the *Rp. palustris* strain is greatly reduced in the presence of CO (FIG. 4B). Thus, the growth of *R. palustris* is really reduced by the inhibition of cytochromes P450 when TBP is present. Assaying of the residual TBP concentration after 21 days of culture shows a considerable decrease in TBP degradation (FIG. 5). This suggests the existence of a correlation between cytochrome P450 inhibition and low TBP degradation yield. This correlation does not exist with the *S. odorifera* strain, for which the CO treatment does not significantly modify the TBP degradation yield.

Example 5

Construction of an *Rp. palustris* Strain Constitutively Overexpressing Cytochrome P450

The 5939 gene of *Rp. palustris* CG009 (all the information concerning this gene can be found on the site http://genome.ornl.gov) encoding a cytochrome P450 was introduced into the same strain.

To do this, a transcriptional fusion of the promoter of the light-harvesting complex II (LH) $\alpha\beta_e$ gene cluster and of the 5939 gene was carried out so as to obtain constitutive expression of the gene in question. The LH$\alpha\beta_e$ promoter is amplified by PCR from 300 bp upstream of the start codon to 68 bp downstream of the latter, using *Rp. palustris* CG009 genomic DNA as template (10), with the following primers:

```
                                         (SEQ ID NO: 1)
5'-GGGGTACCCCTGGGATGTCCGGTATGACA-3'
``` containing a KpnI restriction site (indicated in the sequence in bold), and

```
                                         (SEQ ID NO: 2)
5'-CCCAAGCTTGGGTTGTGGAGCTCTTCCGTTC-3'
```

14 containing a HindIII restriction site (indicated in the sequence in bold).

The PCR amplified fragment is cloned into the cloning vector PGEM-T™ (Promega), to give the plasmid pCB04. The whole 5939 gene is then amplified using the following primers:

```
                                         (SEQ ID NO: 3)
5'-CCCAAGCTTGGGTGAACAACAACGAGGGAGTG-3'
``` containing a HindIII restriction site (indicated in the sequence in bold), and

```
                                         (SEQ ID NO: 4)
5'-CCCGAGCTCGGGCTATGGCGTGGAAATGGA-3'
``` containing a SacI restriction site (indicated in the sequence in bold).

The PCR amplified fragment is digested with HindIII and SacI and ligated into the plasmid pBBR1MCS2 (Kovach et al., 1994) at the same sites, which makes it possible to obtain the plasmid pCB06.

Figure 6:
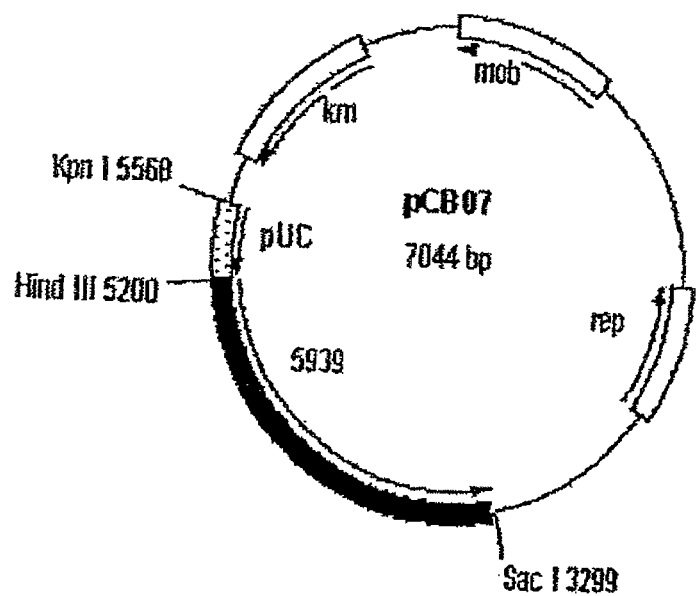
FIG. 6 represents the plasmid pCB07 comprising the gene encoding *Rp. palustris* cytochrome P450, No. 5939, and the $LH\alpha\beta_e$ promoter.

The plasmid pCB04 is digested with KpnI and HindIII, and cloned into the plasmid pCB06 digested with these same restriction enzymes, so as to obtain the plasmid pCB07. The map of the plasmid pCB07 is given in FIG. 6.

In order to overexpress cytochrome P450 in the *Rp. palustris* CG009 strain, the plasmid pCB07 containing the 5939 gene under the control of the LH$\alpha\beta_e$ promoter is transferred, by triparental conjugation using the *E. coli* strains DH5α phe (Eraso, et al., 1994) and HB101 (Boyer et al., 1969) into the *Rp. palustris* CG009 strain so as to obtain the *Rp. palustris* LH5939 strain overexpressing cytochrome P450 (positive clones). These positive clones are selected in a medium containing kanamycin at a concentration of between 20 and 100 μg/ml.

Example 6

Comparative Study of TBP Degradation by Various Cell Extracts

A. Materials and Methods

Extraction and Fractionation of Proteins

The *Rp. palustris* strain, cultured on Hutner medium in the presence or absence of 2 mM of TBP, was harvested at the end of the exponential growth phase by centrifugation at 8000 g for 10 minutes at 4° C. The pellets were washed twice in phosphate buffer, pH 7.2, and resuspended in 20 ml of the same buffer containing a cocktail of protease inhibitors (P8849, Sigma-Aldrich). The cells were ruptured mechanically by passing them three times through a cell press at 16 000 psi, and the bacterial lysate was centrifuged for 20 minutes at 10 000 g in order to remove the cell debris and the intact cells. The crude extract was divided up into 3 fractions. A centrifugation at 200 000 g for 90 minutes at 4° C. was carried out in order to sediment the membranes. The supernatant constituted the soluble protein fraction. In order to dissociate the proteins weakly associated with the membrane, the pellet was resuspended in 2 ml of 2M NaBr buffer containing 200 mM sucrose and 50 mM glycylglycine, at pH 6, and supplemented with a cocktail of protease inhibitors, and then extracted by mild agitation for 30 minutes at 4° C.; the supernatant constituted the fraction enriched in proteins weakly associated with the membrane. The pellet, containing the proteins strongly associated with the membrane, was resuspended in 2 ml of 50 mM Tris-HCl buffer, pH 8, containing 0.5% (vol/lvol) lauryl diaminooxide (LDAO) and supplemented with a cocktail of protease inhibitors. The proteins were solubilized by mild agitation for 60 minutes at 4° C. The resulting extract was centrifuged at 200 000 g for 90 minutes at 4° C. in order to pellet the insoluble materials. The supernatant constitutes the membrane-bound protein fraction. The protein concentration in each extract was determined by the biuret method according to the BSA Protein Assay Reagent kit (Uptima) and using bovine serum albumin as a standard.

B. Results

The TBP degradation tests were carried out with proteins extracted from *Rp. palustris* CGA009. The optimal conditions for the test are as follows: pH 6.5 and 40° C.

The cell extracts are obtained under the conditions disclosed above in the Materials and methods chapter; they are in particular obtained by extraction of the proteins from the *Rp. palustris* strain cultured under microaerobic conditions, in Hutner medium in the presence (induced cultures) or absence (noninduced cultures) of 2 mM of TBP.

Figure 7:
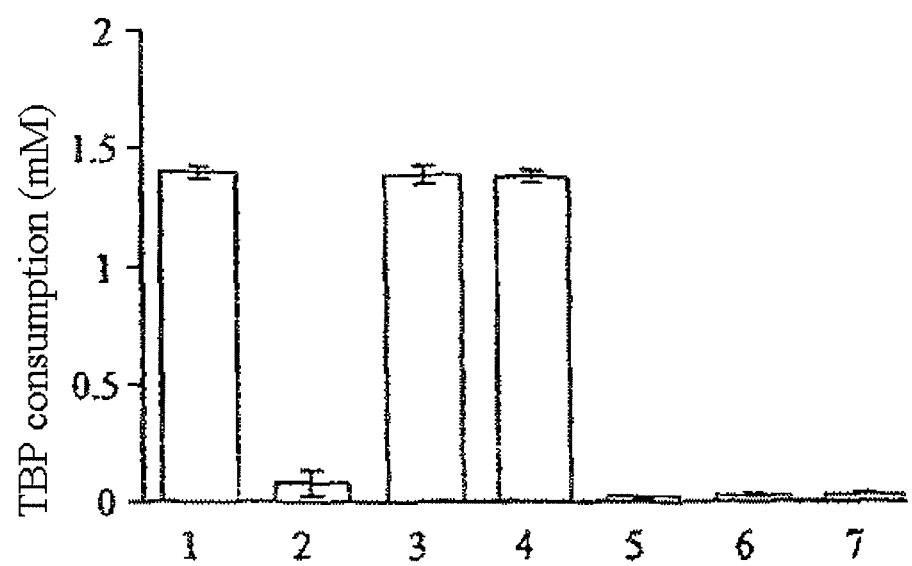
FIG. 7 represents the TBP consumption (in mM) by cell extracts of *Rp. palustris* strains, over a period of 20 hours at 40° C., the initial TBP concentration being 2 mM. The samples studied are total proteins of: (1): CGA009 strain not induced with TBP in the presence of $O_2$; (2): CGA009 strain not induced with TBP in the absence of $O_2$; (3) CGA009 strain induced with TBP in the presence of $O_2$, and (4): ΔpRpa1 strain. The controls are as follows: (5): reaction buffer without protein; (6) boiled crude extract of *Rp. palustris* CGA009, and (7): crude extract of *E. coli* DH5α. The values are means±standard deviations, from three independent experiments.

FIG. 7 shows that 70% of TBP is degraded by cell extracts at 40° C. under aerobic conditions for 20 hours, independently of the possible presence of TBP in the culture medium (FIG. 7: (1) and (3)). An experiment was also carried out under anaerobic conditions. In this case, no degradation is observed (FIG. 7: (2)); this implies that oxygen is necessary in order to degrade TBP, as for whole cells.

The TBP degradation assays were compared with the results obtained from various controls: reaction buffer without protein, boiled crude extract of *Rp. palustris* CGA009 and crude extract of *E. coli* DH5α (FIG. 7: (5), (6) and (7)).

These results show:
that the degradation takes place via an enzymatic process; in fact, no degradation is observed in a certain number of tests (see FIG. 7) and no significant accumulation of TBP is observed in the cells for a culture period of 21 days: there is therefore no sequestration of the nondegraded compound;
the degradation process is oxygen-dependent both in vitro and in vivo. However, there is clearly no stoichiometric correlation between the amount of oxygen and the amount of TBP degraded. The optimal initial $O_2$ concentration is approximately 70 μM, in the microaerobic medium selected;
TBP degradation is a constitutive mechanism of the cell, insofar as the cell extracts of bacteria cultured in the presence or absence of TBP have the same effectiveness; in addition, a subculture obtained from a strain cultured beforehand in a medium containing TBP exhibits the same profile as a subculture obtained from a noninduced culture (growth in a medium in the absence of TBP); the degradation kinetics are identical.

Example 7

Comparative Study of the Kinetics of TBP Degradation in the Presence of Various Concentrations of TBP and by Various Cell Extracts A. Materials and Methods
Kinetic Analyses The kinetic parameters for TBP degradation were calculated from the Michaelis-Menten equation, $V = Vm[S]/(Km+[S])$ where V corresponds to the rate of degradation of TBP and S to the concentration of TBP. This equation was used to adjust the various experimental data for V=f([S]) using a non-linear adjustment method (SigmaPlot). This approach is more accurate than the linear adjustment of the double-reciprocal point (Lineweaver-Burk), due to the variable size of the error bars in the latter. Since the enzymatic activity was assayed in a crude extract system, the kinetic parameters were expressed as apparent TBP concentration for half the maximum activity ($Km_{ap}$) and for the apparent maximum rate ($Vm_{ap}$).

B. Results

Figure 8:
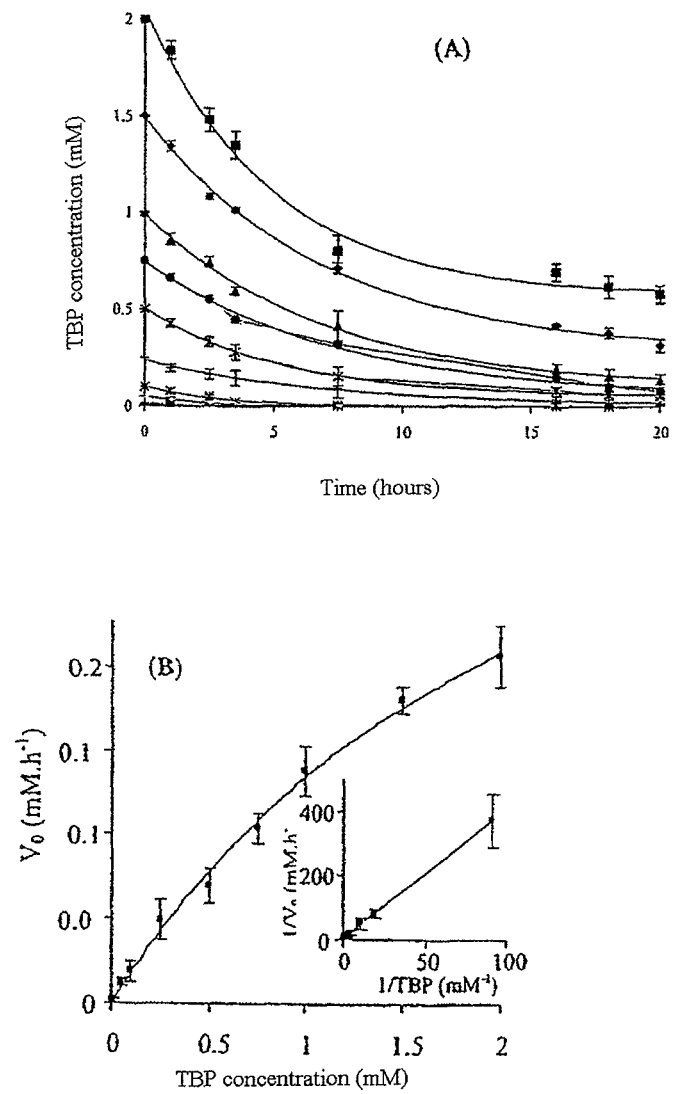
FIG. 8 represents (A): the kinetic of TBP consumption by cell extracts at 40° C. in the presence of various initial concentrations of TBP (in mM); the TBP concentrations are as follows: 0.05 mM (−), 0.1 mM (*), 0.25 mM (+), 0.5 mM (x), 0.75 mM (●), 1 mM (▲), 1.5 mM (♦) and 2 mM (■) The values are means±standard deviations, from three independent experiments. (B): initial degradation rate vs initial TBP concentration in a crude cell extract (data obtained in A). The line represents the best Michaelis-Menten equation correspondence. A Lineweaver-Burk diagram is illustrated in the insert.

FIG. 8A shows the kinetics of TBP degradation by cell extracts as a function of various TBP concentrations: 2, 1.5, 1, 0.75, 0.5, 0.25, 0.1 and 0.05 mM.

FIG. 8B shows the best correspondence of the Michaelis-Menten equation with $Vm_{ap}$ and $Km_{ap}$ values, respectively, of: 0.48±0.04 mM·h$^{-1}$ and 2.6±0.4 mM.

The analysis of the degradation kinetics carried out using cell extracts is consistent with the Michaelis-Menten equation. This makes it possible to estimate the $Km_{ap}$ and the $Vm_{ap}$, although the maximum rate cannot be reached under the experimental conditions (low solubility of TBP in water).

A $Km_{ap}$ of 2.6 mM indicates that the enzymatic system has a moderate apparent affinity for TBP. The $Vm_{ap}$ was 0.48 mM·h$^{-1}$.

For TBP concentrations of between 2 and 0.5 mM, the kinetics exhibit significant slowing, after a time, which is probably due to inhibition by the product (biphasic curve). For TBP concentrations of less than 0.5 mM, the kinetics follow a monophasic curve (see also Example 2).

Example 8

Influence of Cofactors on the Degradation of TBP by Cell Extracts

Figure 9:
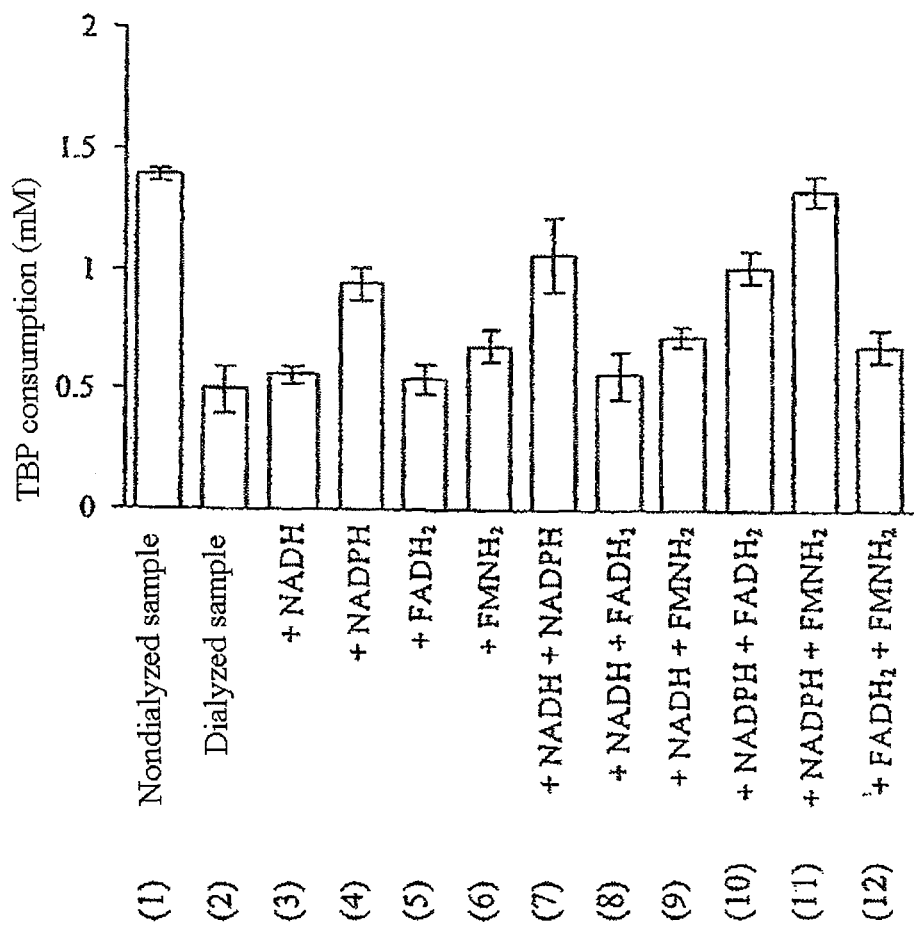
FIG. 9 represents the degradation of TBP by dialyzed or nondialyzed cell extracts, over a period of 20 hours at 40° C., the initial concentration of TBP being 2 mM. The cofactors are added at a final concentration of 10 μM. The values are means±standard deviations, from three independent experiments.

A crude extract, obtained under the conditions described in Example 6, is dialyzed so as to reduce the concentration of low molecular weight molecules. After dialysis, the degradation of TBP is decreased by a factor of 3, in comparison with the nondialyzed control (FIG. 9, (1) and (2)). Under these conditions, the effect of various cofactors was tested: NADH, NADPH, $FMNH_2$ and $FADH_2$. On nondialyzed cell extracts, the addition of these cofactors does not significantly enhance the TBP degradation. On the other hand, the degradation by dialyzed samples is increased by the addition of NADPH or of $FMNH_2$ (FIG. 9, (4) and (6)). The combination of these two cofactors completely restores the degradation activity observed with the nondialyzed samples.

Example 9

Degradation of TBP by Protein Fractions

In order to be able to localize the enzymatic activity involved in the degradation of TBP by *Rp. palustris*, a crude extract is fractionated into three protein fractions: soluble fraction, fraction weakly associated with the membrane and membrane-bound fraction; these various fractions are obtained under the conditions disclosed in Example 6. The TBP degradation tests are carried out under the conditions disclosed in Example 2.

Figure 10:
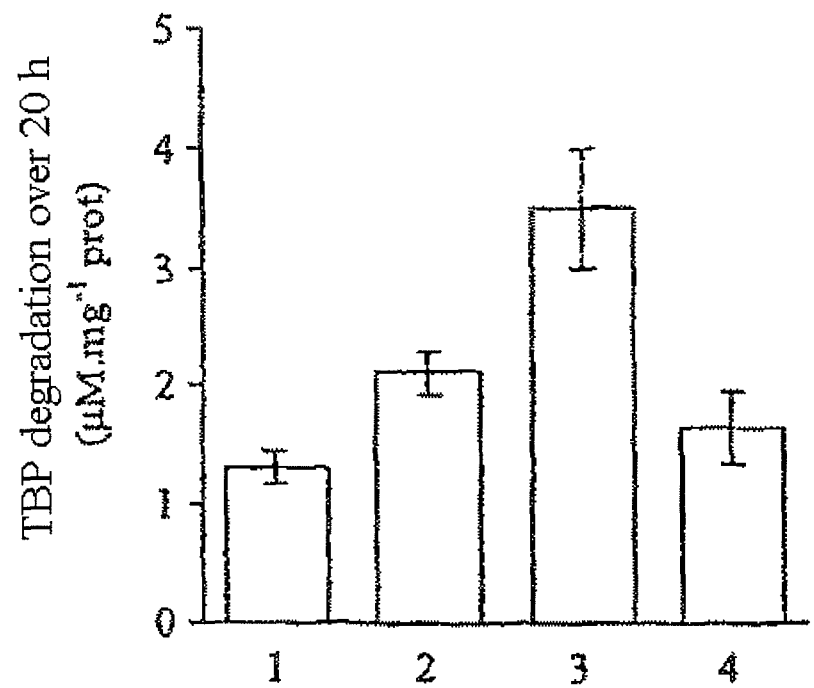
FIG. 10 illustrates the amount of TBP degraded (using an initial concentration of 2 mM) over a period of 20 hours at 40° C., by various fractions of cell extracts: (1): crude extract; (2) soluble fraction; (3) protein fraction weakly associated with the membrane and (4) membrane-bound protein fraction. The values are a function of the weight of protein present in each case and are means±standard deviations, from five independent experiments.

FIG. 10 shows that the degradation activities more particularly located in the fraction of proteins weakly associated with the membrane, with 3.5 μM of TBP degraded.mg of proteins$^{-1}$, compared with the amounts degraded, respectively, by the total protein fraction (1.2 μM of TBP degraded.mg of proteins$^{-1}$), the soluble fraction (2 μM of TBP degraded.mg of proteins$^{-1}$) and the membrane-bound fraction (1.65 μm of TBP degraded.mg of proteins$^{-1}$).

The proteins involved in TBP degradation are weakly associated with the membrane. The activity is both NADPH-dependent and FMNH$_2$-dependent and confirms the role of cytochrome P450 in the TBP degradation activity.

Example 10

Activity of an Rp. palustris Strain Devoid of the Endogenous Plasmid pRpa1

A. Materials and Methods
Molecular Techniques

The isolation of the plasmids was carried out using the NucleoSpin Plasmid kit (Macherey-Nagel) according to the supplier's instructions. The isolation of genomic DNA was carried out using the NucleoSpin Tissue kit (Macherey-Nagel) according to the supplier's instructions.

During the conjugation processes, the plasmids were obtained by triparental crossing using the E. coli strains DH5α phe (donor) containing the plasmid pMG105, and HB101 (helper), to the Rp. palustris strain (accepter).

The E. coli cells were cultured in LB medium+Km until the OD$_{660}$ value reached 1.5, and the Rp. palustris cells were cultured on the Hutner medium until the OD$_{660}$ value reached 1 (overnight culture). The "donor, helper and accepter" bacteria (100 µl, 10 µl and 1 ml respectively) were washed and combined on a dish of Hutner medium. This dish was incubated at 30° C. for 16 hours. The bacteria were resuspended in 1 ml of PM medium, plated out onto PM+Km dishes, and incubated for 4 days either under aerobic conditions or under microaerobic conditions.

Plasmid Elimination Experiments

To eliminate the plasmid pRpa1, the plasmid pMG105 (11), a cloning vector with a Km-resistance gene, which has the same origin of replication as pRpa1, was introduced by crossing into R. palustris. The transconjugants carrying pMG105 were selected on PM+Km dishes. Generally, the Km-resistant bacteria have lost pRpa1. The strains carrying pMG105 were cultured on a medium without Km in order to expel this plasmid after several subcultures, and the resulting strain without plasmid is conserved as Rp. palustris ΔpRpa1. Each step of the elimination experiment is verified by isolation of the plasmid. The R. palustris ΔpRpa1 bacteria are tested for their ability to degrade TBP.

B. Results

A plasmid extraction showed that Rp. palustris comprises an endogenous plasmid (pRpa1, 9.8 kb). This characteristic was confirmed by sequencing the Rp. palustris genome (12).

The growth, the morphological form and the pigmentation of the colonies are identical in the ΔpRpa1 strain and in the wild-type strain. Rp. palustris is naturally resistant to gentamycin (50 µg·ml$^{-1}$) and the plasmid-free strain grows in the presence of this antibiotic, like the wild-type strain. The plasmid-free strain also grows in a medium containing TBP, like the wild-type strain, and exhibits TBP degradation kinetics similar to those of the wild-type strain. This indicates that the enzymes involved in TBP degradation by Rp. palustris are not encoded by genes carried by the endogenous plasmid, but rather by the chromosomal DNA.

Rp. palustris is effective in the depollution process, as is the plasmid-free strain; the latter may also constitute a tool for determining the plasmid or chromosomal localization of genes involved in other degradation pathways.

BIBLIOGRAPHICAL REFERENCES

1. Thomas R. A. et al., Appl Microbiol Biotechnol., 1998, 49, 202-209.
2. Thomas R. A. P. et al., Biotechnol Techn., 1997, 11, 781-785.
3. Thomas, R. A. P. et al., Environ. Sci. and Biotechnol., 1996, 30, 2371-2375.
4. Thomas R. A. P. et al., FEMS Microbiology Lett., 1997, 155, 155-159.
5. Owen S. et al., Appl Biochem Biotechnol., 1992, 34/35, 693-707.
6. Clayton R., K., Biochim. Biophys. Acta., 1960, 37, 503-512.
7. Boyer H. W. et al., J. Mol. Biol., 1969, 41, 459-72.
8. Eraso J. M. et al., J. Bacteriol., 1994, 176, 32-43.
9. Kovach M. E. et al., Biotechniques, 1994, 16, 800-2.
10. Tadros M. H. et al., Eur. J. Biochem., 1993, 217, 867-75.
11. Inui M et al., Appl. Environ. Microbiol., 2000, 66, 54-63
12. Larimer F. et al., Nat. Biotechnol., 2004, 22, 55-61

The invention claimed is:

1. A method of treating or purifying liquid waste loaded with tributyl phosphate (TBP), comprising the steps of:
   (1) bringing said liquid waste into contact with at least one TBP-resistant purple non-sulfur photosynthetic bacterial strain selected from the group consisting of *Rhodopseudomonas palustris* (*Rp. palustris*), *Rhodospirillum rubrum* (*Rs. rubrum*), *Rhodobacter capsulatus* (*Rb. capsulatus*) and *Rhodobacter sphaeroides* (*Rb. sphaeroides*), under conditions that allow the degradation of the TBP present in said waste; and
   (2) recovering purified liquid effluents, wherein the TBP-resistant purple non-sulfur bacterial strains are selected from the group consisting of the strains *Rp. palustris* CGA009 No. ATCC BAA-98, No. ATCC 17002, No. ATCC 17007, No. DSM 8283, No. DSM 126, No. DSM 7375, No. DSM 131, No. DSM 25, No. DSM 124 and No. DSM 130, the strain *Rs. rubrum* S1 No. ATCC 11170, the strain *Rb. capsulatus* Saint Louis No. ATCC 23782 and the strain *Rb. sphaeroides* 2.4.1. No. ATCC 17023.

2. The method as claimed in claim 1, wherein the step (1) is carried out under conditions of microanaerobiosis.

3. The method as claimed in claim 1, wherein said TBP-resistant bacterial strain used in the step (1) of the method is selected from the group consisting of *Rp. palustris* and *Rs. rubrum*.

4. The method as claimed in claim 1, wherein the step (1) comprises the use of a mixture of TBP-resistant purple non-sulfur bacterial strains comprising at least one strain selected from the group consisting of *Rhodospirillum rubrum* (*Rs. rubrum*) and *Rhodopseudomonas palustris* (*Rp. palustris*) and at least one other strain selected from the group consisting of *Rhodobacter capsulatus* (*Rb. capsulatus*) and *Rhodobacter sphaeroides* (*Rb. sphaeroides*).

5. The method as claimed in claim 1, wherein the step (1) is carried out at a temperature of between 10° C. and 37° C., at a pH of between 5.5 and 8.5, and for at least 15 days.

6. The method as claimed in claim 1, wherein the amount of TBP in said liquid waste before treatment is between 0.01 mM and 1 M.

7. The method as claimed in claim 1, wherein the amounts of bacteria inoculated into the medium to be treated in the step (1) are between $10^4$ and $10^{10}$ bacteria per ml of medium to be treated.

8. The method as claimed in claim 1, wherein, during the step (1), an additional carbon source is added to the medium to be treated.

9. The method as claimed in claim 8, wherein said additional carbon source is a buffered solution containing a yeast extract at a concentration of between 0.1 and 10 g/l or one of the following organic salts: succinate, glutamate, benzoate, malate or fumarate at a concentration of between 2 and 20 mM, and growth factors, including at least biotin and para-aminobenzoic acid each at a concentration of between 2 and 40 µg/l.

10. The method as claimed in claim 1, wherein prior to said bringing into contact according to the step (1), the TBP-resistant purple non-sulfur bacteria are selected by culturing on medium containing at least 12 µM of TBP.

11. A method of following or monitoring the degradation of TBP in liquid waste, which method comprises:
   carrying out the method of treating liquid waste loaded with TBP as claimed in claim 1, and then
   taking a sample of treated medium at least at time t+15 days and measuring, in said sample taken, the concentration of residual TBP.

12. A kit for carrying out the method of treatment as claimed in claim 1, comprising at least one TBP-resistant purple non-sulfur photosynthetic bacterial strain chosen from the group consisting of *Rp. palustris*, *Rs. rubrum*, *Rb. capsulatus* or *Rb. sphaeroides* and also said bacterial strains modified so as to overexpress cytochrome P450.

13. The method of claim 1, wherein the at least one TBP-resistant purple non-sulfur photosynthetic bacterial strain has been modified so as to express cytochrome P450.

14. The method as claimed in claim 1, wherein prior to said bringing into contact according to the step (1), the TBP-resistant purple non-sulfur bacteria are selected by culturing on medium containing at least 1 mM of TBP.

* * * * *

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: PCR primer

<400> SEQUENCE: 1
ggggtacccc tgggatgtcc ggtatgaca                29

<210> SEQ ID NO 2
<211> LENGTH: 31
<212> TYPE: DNA
<213> ORGANISM: Artificial Sequence
<220> FEATURE:
<223> OTHER INFORMATION: PCR primer

<400> SEQUENCE: 2
cccaagcttg ggttgtggag ctcttccgtt c              31

```
<210> SEQ ID NO 3
<211> LENGTH: 32
<212> TYPE: DNA
<213> ORGANISM: Artificial Sequence
<220> FEATURE:
<223> OTHER INFORMATION: PCR primer

<400> SEQUENCE: 3
cccaagcttg ggtgaacaac aacgagggag tg                                    32

<210> SEQ ID NO 4
<211> LENGTH: 30
<212> TYPE: DNA
<213> ORGANISM: Artificial Sequence
<220> FEATURE:
<223> OTHER INFORMATION: PCR primer

<400> SEQUENCE: 4
cccgagctcg ggctatggcg tggaaatgga                                       30
```